United States Patent [19]

Feyen et al.

[11] Patent Number: 5,230,892
[45] Date of Patent: Jul. 27, 1993

[54] SOLID FORMULATIONS

[75] Inventors: Peter Feyen, Mettmann; Uwe Priesnitz, Solingen; Raphael Wieschollek, Leverkusen; Wolfgang Thielert, Odenthal; Stefan Dutzmann, Hilden; Dieter Feucht, Monheim; Ulrike Wachendorff-Neumann, Monheim, all of Fed. Rep. of Germany

[73] Assignee: Bayer Aktiengesellschaft, Leverkusen, Fed. Rep. of Germany

[21] Appl. No.: 911,992

[22] Filed: Jul. 10, 1992

Related U.S. Application Data

[63] Continuation of Ser. No. 746,393, Aug. 16, 1991, abandoned.

[30] Foreign Application Priority Data

Aug. 24, 1990 [DE] Fed. Rep. of Germany ....... 4026704
Jun. 22, 1991 [DE] Fed. Rep. of Germany ....... 4120694

[51] Int. Cl.$^5$ ................. A01N 25/14; A01N 25/30; A01N 37/18; A01N 43/40
[52] U.S. Cl. ........................ 424/409; 424/405; 514/723; 514/724; 514/277
[58] Field of Search ............... 424/409, 405; 514/723, 514/724

[56] References Cited

U.S. PATENT DOCUMENTS

| H303 | 7/1987 | Malik et al. | 514/85 |
|---|---|---|---|
| 4,328,026 | 5/1982 | Kliegman et al. | 71/86 |
| 4,723,984 | 2/1988 | Holmwood et al. | 71/76 |
| 4,759,877 | 7/1988 | Hildreth et al. | 252/547 |
| 4,946,654 | 8/1990 | Uhlemann et al. | 422/140 |
| 5,013,352 | 5/1991 | Markley et al. | 71/94 |

FOREIGN PATENT DOCUMENTS 6709022 1/1968 Netherlands .
8900079 1/1989 World Int. Prop. O. .

OTHER PUBLICATIONS

Chemical Control of Insects by T. F. West & J. Eliot Hardy p. 22 1961 Chapman & Hall, Ltd. London, Publishers.
Chemical Abstracts #109 (5):33080s, 1988 Muraoka et al. Influences of Insecticides, Fungicides and Foliar Application of Fertilizers on the Control Effect of a Caricides to the Citrus Mite, Panonychus Citri (McGregor).
87:145346/21 (Chinoin Gyogyszer), "Granulated plant protecting agent . . . ", Derwent Chemical Patents Index, Abstr. Journal, Jul. 1987 HU-A-T 041 204.

Primary Examiner—Thurman K. Page
Assistant Examiner—Neil Levy
Attorney, Agent, or Firm—Sprung, Horn, Kramer & Woods

[57] ABSTRACT

New solid formulations of
A) at least one agrochemical active compound,
B) at least one additive from the groups mentioned in the description,
C) at least one dispersant,
D) at least one carrier and
E) if appropriate, further active compounds and/or additives, a process for preparing the solid formulations and their use for treating plants.

A new device for preparing new granules.

19 Claims, 1 Drawing Sheet

SOLID FORMULATIONS

This application is a continuation of application Ser. No. 746,393, filed Aug. 16, 1991, now abandoned.

The present invention relates to new solid formulations based on agrochemical active compounds, to processes for the preparation of the solid formulations and to their use as agents for treating plants.

Figure 1:
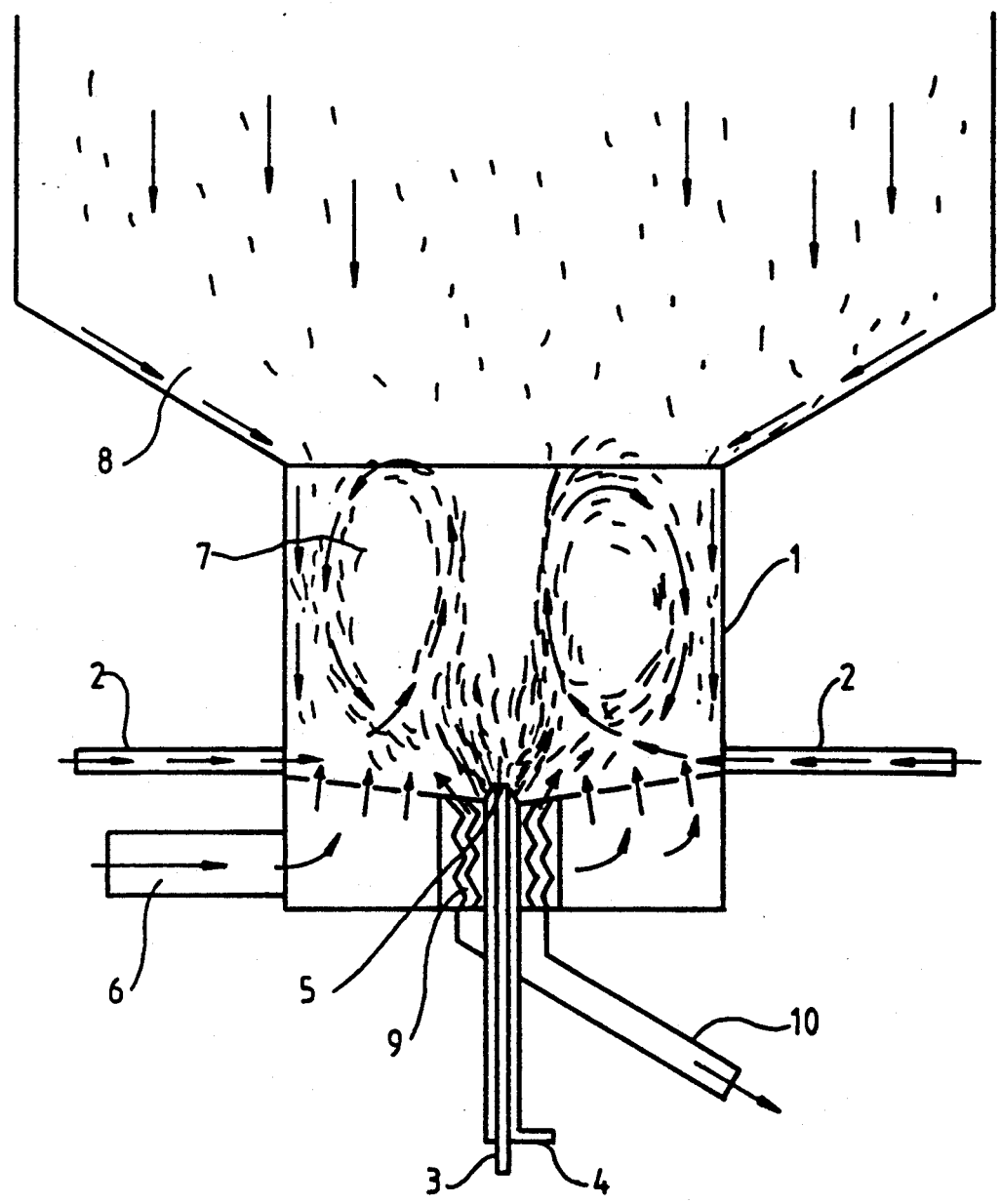
FIG. 1 shows a fluidised bed granulator for preparing the solid formulations.

It has already been disclosed that agrochemical active compounds can be used in the form of solid formulations, such as granules or powders. However, the activity of such preparations is not always entirely satisfactory. For example, it is in some cases less powerful than that of corresponding emulsifiable concentrates.

In particular, it has already been disclosed that 1-(4-chlorophenyl)-4,4-dimethyl-3-(1,2,4-triazol-1-yl-methyl)-pentan-3-ol has fungicidal properties and can be converted into customary formulations (cf. EP-OS (European Published Specification) 0,040,345). Thus, solid formulations, such as granules or powders, which contain the above-mentioned active compound, can also be produced. The activity and the compatibility of these conventional solid formulations, however, is not always entirely satisfactory.

Furthermore, the production of granules containing agrochemical active compounds by the fluidised-bed process has also been described (cf. EP-OS (European Published Specification) 0.163,836). Thus, it is also possible using this method, to obtain granules in which 1-(4-chlorophenyl)-4,4-dimethyl-3-(1,2,4-triazol-1-yl-methyl)-pentan-3-ol is present as the active component. However, the activity of these formulations too, leaves something to be desired in some cases.

New solid formulations of
A) at least one agrochemical active compound,
B) at least one additive from the groups comprising
   polyethoxy-isotridecylalcohol having an average of 6 ethylene oxide units per molecule, or
   alkylaryl-polyethoxyethanol phosphoric acid esters, or
   the N-alkyl-lactams of the formula

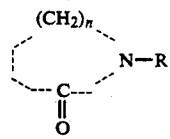

(II)

in which
R represents alkyl having 6 to 18 carbon atoms and
n represents the numbers 3, 4 or 5, or
the N,N-dimethyl-alkylcarboxamides of the formula

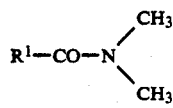

(III)

in which
R$^1$ represents alkyl having 5 to 11 carbon atoms,
C) at least one dispersant,
D) at least one carrier and
E) if appropriate, further active compounds and/or additives,
have now been found.

Furthermore, it has been found that the new solid formulations can be prepared by either
a) introducing a solution of at least one agrochemical active compound and, if appropriate, additives in at least one additional compound from amongst the groups mentioned under (B) and
a mixture of at least one dispersant and at least one carrier and, if appropriate, further agrochemical active compounds and/or additives,
separately into a fluidised-bed granulator, granulating the mixture until a granular product has formed, and discharging the granules from the fluidised-bed granulator, if appropriate after spraying with water followed by drying, or
b) introducing a mixture of at least one dispersant and at least one carrier and, if appropriate, agrochemical-active compounds and/or additives into a mixer,
spraying into the mixer a solution of at least one agrochemical active compound and, if appropriate, additives in at least one additional compound from amongst the groups mentioned under (B) until a product having the desired particle size is formed and
discharging the resulting solid formulation from the mixer, if appropriate, after previously spraying with water followed by drying,
and, if appropriate, subsequently grinding the resulting solid formulations.

Furthermore, it has been found that the solid formulations according to the invention can be employed very successfully as agents for treating plants and have excellent biological properties.

Finally, a new device for preparing the new granules has been found. The device essentially consists of a fluidised-bed granulator which comprises
one or more feed pipes for feeding a solid phase to the fluidised bed,
one or more two-fluid nozzles for feeding and for atomising a liquid phase,
one or more feed pipes for feeding fluidising gas and
one or more counterflow gravity classifiers for discharging granules.

It must be considered extremely surprising that the solid formulations according to the invention in all cases have superior biological properties to the corresponding solid formulations hitherto known. Thus, for example, the solid formulations according to the invention, based on 1-(4-chlorophenyl)-4,4-dimethyl-3-(1,2,4-triazol-1-yl-methyl)-pentan-3-ol can be used considerably more effectively for combating phytopathogenic fungi than the solid formulations known from the prior art and which also contain the same active compound.

Agrochemical active compounds which can be contained in the solid formulations according to the invention are all those substances which are conventionally suitable for treating plants. Suitable active compounds are not only substances which are solid at room temperature but also those which are liquid at room temperature. The only precondition for the use of liquid components is that they must be capable of being applied to solid carrier substances, if appropriate, with powdering. The active components can be soluble or insoluble in water. They must have such stability that they do not undergo any major decomposition while the process according to the invention is being carried out or during the use of the resulting solid formulations.

In the present case, agrochemical active compounds are to be understood to be active compounds which are customarily usable in crop protection. They preferably include insecticides, acaricides, nematicides, fungicides, herbicides, growth regulators and fertilisers. The following may be mentioned as specific examples of such active compounds.

1-(4-chlorophenyl)-4,4-dimethyl-3-(1,2,4-triazol-1-yl-methyl)-pentan-3-ol (tebuconazole),
1-(4-chlorophenoxy)-3,3-dimethyl-1-(1,2,4-triazol-1-yl)-butan-2-ol (triadimenol),
1-(4-chlorophenoxy)-3,3-dimethyl-1-(1,2,4-triazol-1-yl)-butan-2-one (triadimefon),
1-(4-phenyl-phenoxy)-3,3-dimethyl-(1,2,4-triazol-1-yl)-butane-2-ol (bitertanol),
N,N-dimethyl-N'-phenyl-(N'-fluorodichloromethylthio)-sulphamide (dichlofluanid),
N,N-dimethyl-(N'-fluorodichloromethylthio)-N'-(4-methyl-phenyl)-sulphamide (tolylfluanid),
N-trichloromethylmercapto-4-cyclohexene-1,2-dicarboxamide (captan),
N-(1,1,2,2-tetrachloroethyl-sulphenyl)-cis-4-cyclohexene-1,2-dicarboxamide (captafol),
N-trichloromethylthio-phthalimide (folpet),
N-dodecyl-quanidine acetate (dodine),
tetrachloro-isophthalonitrile (chlorothalonil),
4,5,6,7-tetrachlorophthalide,
zinc ethylene-bis-dithiocarbamate (zineb),
manganese ethylene-bis-dithiocarbamate (maneb),
zinc ethylene-bis-dithiocarbamate/manganese ethylene-bis-dithiocarbamate (mancozeb),
zinc propylene-1,2-bis-dithiocarbamate (propineb),
1-[3-(4-(1,1-dimethylethyl)-phenyl)-2-methylpropyl]-piperidine (fenpropidin),
N-tridecyl-2,6-dimethyl-morpholine (tridemorph),
N-dodecyl-2,6-dimethyl-morpholine (aldimorph),
2-[2-(2,4-dichlorophenyl)-2-(2-propenyloxy)-ethyl]-imidazole (imazalil),
N-[2-(2,4,6-trichlorophenoxy)-ethyl]-N-propyl-1H-imidazole (prochloraz),
N-(3,5-dichlorophenyl)-1,2-dimethyl-cyclopropane-1,2-dicarboximide (procymidone),
2-methoxycarbamoyl-benzimidazole (carbendazim),
methyl 1-(butylcarbamoyl)-2-benzimidazolecarbamate (benomyl),
2,4-dichloro-6-(2'-chlorophenyl-amino)-1,3,4-triazine (anilazine),
bis-(8-guanidino-octyl)-amine triacetate (guazatine),
1-(4-chlorobenzyl)-1-cyclopentyl-3-phenyl-urea (pencycuron),
6-methyl-2-oxo-1,3-dithiolo-[4,5-b]-quinoxaline (chinomethionat),
trans-4-(4-chlorophenyl)-N-cyclohexyl-4-methyl-2-oxo-3-thiazolidin-carboxamide (hexythiazox),
1-(4-fluorophenyl)-1-(1,2,4-triazol-1-yl-methyl)-2-(2-chlorophenyl)-oxirane,
2-(2,4-dichlorophenyl)-1-(1,2,4-triazol-1-yl)-pentane (penconazole),
1-[2-(2,4-dichlorophenyl)-4-propyl-1,3-dioxolan-2-yl-methyl]-1H-(1,2,4-triazole) (propiconazole),
1-(2-[2-chloro-4-(4-chlorophenoxy)-phenyl]-4-methyl-(1,3-dioxolan-2-yl)-methyl]-1H-(1,2,4-triazole),
1-(2,4-dichlorophenyl)-4,4-dimethyl-2-(1,2,4-triazol-1-yl)-pentan-3-ol (diclobutrazole),
1-(2-chlorophenyl)-2-(1-chloro-cycloprop-1-yl)-3-(1,2,4-triazol-1-yl)-propan-2-ol,
1-cyclohexyl-4,4-dimethyl-3-hydroxy-2-(1,2,4-triazol-1-yl)-pent-1-ene (triapenthenol),
2-isopropoxy-phenyl-N-methyl-carbamate,
4-amino-6-(1,1-dimethyl-ethyl)-3-methylthio-1,2,4-triazin-5(4H)-on (metribuzin),
3-methyl-4-amino-6-phenyl-1,2,4-triazin-5(4H)-on (metamitron),
N-benzthiazolyl-N-methyl-N'-methyl-urea,
3-methoxycarbonyl-aminophenyl-N-(3'-methyl-phenyl)carbamate,
N-(4-trifluoromethoxy-phenyl)-N'-(2-chloro-benzoyl-)urea,
1-[4-(2-chloro-1,1,2-trifluoroethoxy)-phenyl]-3-(4-phenyl-1,2,5-oxadiazol-3-yl)-urea,
2-ethoxy-2,3-dihydro-3,3-dimethyl-5-benzofuranylmethansulfonate.

1-(4-Chlorophenyl)-4,4-dimethyl-3-(1,2,4-triazol-1-yl-methyl)-pentan-3-ol of the formula

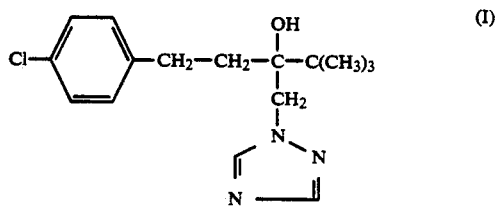

is particularly preferred.

This active compound and its use as a fungicide are known (cf. EP-OS (European Published Specification) 0,040,345).

The active compound of the formula (I) can be contained in the solid formulations according to the invention either as the sole active component or in admixture with other agrochemical active compounds.

In the solid formulations according to the invention, at least one of the substances mentioned under (B) is contained as an additional substance. The following are preferably suitable:

polyethoxy-iso-tridecyl alcohol having an average of 6 ethylene oxide units per molecule,
alkylaryl-polyethoxyethanol phosphoric acid ester, commercially available under the name "Blendex ®",
N-alkyl-lactams of the formula (II) in which
R represents alkyl having 8 to 14 carbon atoms and
n represents the numbers 3, 4 or 5, and
moreover, individual N,N-dimethyl-alkylcarboxamides of the formula (III), or mixtures thereof.

Particularly preferred N-alkyl-lactams are those substances of the formula (II) in which
R represents alkyl having 8, 10 or 12 carbon atoms and
n represents the numbers 3, 4 or 5.

The following may be mentioned as examples of N-alkyl-lactams of the formula (II):
N-dodecyl-caprolactam
N-decyl-caprolactam
N-octyl-caprolactam
N-dodecyl-pyrrolidone
N-decyl-pyrrolidone
N-octyl-pyrrolidone
N-dodecyl-valerolactam
N-decyl-valerolactam
N-octyl-valerolactam.

Also particularly preferred is the mixture of N,N-dimethyl-alkylcarboxamides of the formula (III) which is known under the tradename Hallcomid and which comprises, on average, 5% N,N-dimethyl-hexanecarboxamide, 50% N,N-dimethyl-octanecarboxamide, 40% N,N-dimethyl-decanecarboxamide and 5% N,N-dimethyl-dodecanecarboxamide.

The additional substances present in the solid formulations according to the invention are known (cf. J. Org. Chem. 18, 1087 (1953); Ann. Chem. 596, 203 (1955); J. Amer. Chem. Soc. 69, 715 (1947); DE-AS (German Published Specification) 1,160,268; EP-OS (European Published Specification) 0,077,078, WO 88/00 184 and Farm Chemicals Handbook 1990, C 44).

Suitable dispersants in the case of solid formulations according to the invention are all substances which have appropriate surface-active properties and which can customarily be employed for such purposes. The following are preferred: ligninsulphonates such as lithium salts, sodium salts, potassium salts, magnesium salts, calcium salts and ammonium salts of ligninsulphonic acid, furthermore condensation products of aryl- or alkylarylsulphonic acids and formaldehyde, such as condensation products of sulphonated ditolyl ether and formaldehyde, and salts thereof, as well as addition products of ethyleneoxide and fatty acid esters and salts thereof.

Suitable carriers in the case of the solid formulations according to the invention are all solid substances which have a large surface area and/or high absorbency and which can customarily be used in granules and powders. The following are preferred: ground natural minerals such as kaolins, clays, talc, chalk, quartz, attapulgite, montmorillonite or diatomacious earth, and ground synthetic minerals such as highly-disperse silica, alumina and silicates, and furthermore salts such as potassium sulphate, potassium carbonate and sodium hydrogen carbonate.

Suitable additives which can be contained in the solid formulations according to the invention are binders, preservatives, colorants, acids and granulation liquids.

Binders which can be contained are all binders (tackifiers) which are customarily present in water-dispersible solid formulations. The following are preferably suitable in this context: methylcellulose, sugars, dextrin, starch, alginates, glycols, polyvinyl pyrrolidone, ligninsulphonate, gum arabic, polyvinyl alcohol and polyvinyl acetate.

Examples of preservatives which can be contained in the solid formulations according to the invention are 2-hydroxybiphenyl, sorbic acid, p-hydroxybenzaldehyde, methyl p-hydroxybenzoate, benzaldehyde, benzoic acid and propyl p-hydroxybenzoate.

Colorants which may be mentioned as suitable additives are inorganic pigments such as iron oxide, titanium dioxide and Prussian blue, and organic dyestuffs such as alizarin, azo and metal phthalocyanine dyestuffs.

An example of an acid which may be mentioned as a suitable additive is p-tolyl-sulphonic acid.

Examples of granulation liquids which can be contained in the solid formulations according to the invention are water, organic solvents or mixtures of water and organic solvents. Preferred organic solvents which are suitable in this context are alcohols such as ethanol and glycol, halogenohydrocarbons such as methylene chloride, and ethers such as dioxane and tetrahydrofuran. Water is particularly preferred as granulation liquid.

In the solid formulations according to the invention, the percentage contents of the components can be varied within substantial range. In general, the content of agrochemical active compounds is between 5 and 90% by weight, preferably between 10 and 50% by weight. The amount of additive is generally 5 to 75% by weight, preferably 10 to 70% by weight. The amount of dispersant is generally between 1 and 30% by weight, preferably between 5 and 25% by weight; and the amount of carrier is generally between 10 and 50% by weight, preferably between 15 and 45% by weight. The additional compounds are generally contained in amounts of between 10 and 70% by weight, preferably between 20 and 50% by weight, and the amount of granulation liquid is generally between 0 and 3.5% by weight.

When carrying out the process according to the invention by means of variants (a) or (b), all those components can preferably be used as being preferred which have already been mentioned in connection with the description of the solid formulations according to the invention.

For carrying out the process according to the invention by means of variant (a), a solution of at least one agrochemical active compound and, if appropriate, additional substances in at least one additive is first prepared. For this purpose, the components are stirred with each other at temperatures between 10° C. and 100° C., preferably between 20° C. and 90° C., so that a liquid phase results. Accordingly, the liquid phase is a melt or a true solution.

Furthermore, a solid mixture is prepared by mixing at least one dispersant and, if appropriate, one or more agrochemical active compounds and/or additives with at least one solid carrier in such a ratio that the resulting mixture is in the solid phase. This mixture of solid substances is homogenised using customary processes.

For carrying out the process according to the invention by means of variant (a), the liquid and the solid phase are introduced separately into a fluidised-bed granulator. In general, a procedure is followed in which the solid, finely pulverulent phase is passed into the granulator through one or more inlets and fluidised with the aid of a stream of gas. The liquid phase is also sprayed into the granulator through one or more separate nozzles. The liquid phase is preferably added via one or more two-fluid nozzles which are constructed in such a way that the liquid phase is transported through a first line and a stream of gas (atomising gas) is fed in through a second line. Both streams meet each other at the end of the nozzle in such a way that, with the aid of the atomising gas, the liquid phase is sprayed into the fluidised bed in the form of small droplets, and there meets the particles of the solid phase.

If appropriate, post-granulation can be carried out by spraying on water. To remove water and/or other solvents, the granules can be dried with the aid of the stream of gas for fluidisation.

When carrying out the process according to the invention by means of variant (a), the temperatures can be varied within a substantial range. For example, the process is carried out using a liquid phase whose temperature is between 10° C. and 100° C., preferably between 20° C. and 90° C. The solid phase is fed in at temperatures between 10° C. and 50° C., preferably between 20° C. and 40° C. The temperature of the stream of gas for fluidisation is between 20° C. and 250° C., preferably between 40° C. and 200° C. The temperature of the stream of gas for atomisation, which enters through the two-fluid nozzle, is between 0° C. and 100° C., preferably between 10° C. and 90° C.

To produce the fluidised bed, all gases which are customarily employed for such purposes can be used. Air or nitrogen are preferably suitable.

For spraying in the liquid phase via one or more two-fluid nozzles, it is also possible to use all gases which are customary for such purposes. Air or nitrogen are preferably suitable.

The finished granules can be discharged from the granulator via customary withdrawal devices. Countercurrent gravity classifiers are preferably used.

The product obtained can subsequently be post-granulated and/or dried and/or ground.

When variant (a) is used, the process according to the invention can be carried out continuously or batchwise.

The device for preparing the granules according to variant (a) of the invention is a fluidised-bed granulator which differs from the previously known apparatuses of this type essentially by the fact that the liquid phase and the finely pulverulent solid phase are fed separately into the fluidised bed.

One or more feedpipes for the solid phase are located in the lower area of the fluidised bed, preferably in the side wall of the apparatus, slightly above the inlet-flow bottom. To feed the liquid phase, there exist one or more two-fluid nozzles which are preferably arranged at the inlet-flow bottom. The two-fluid nozzles are constructed in such a way that the liquid phase is transported through the first feedpipe and a stream of gas (atomising gas) is fed through a second feedpipe. One or more feedpipes for introducing fluidised gas are arranged below the inlet-flow bottom. Finally, the device contains one or more counterflow gravity classifiers for discharging granules. The counterflow gravity classifiers are preferably built into the inlet-flow bottom. Preferred counterflow gravity classifiers which are suitable are so-called zig-zag classifiers.

Variant (a) of the process according to the invention is preferably carried out in a fluidised-bed granulator as shown in FIG. 1 in the form of a diagram. In this figure, 1 denotes the wall of the granulator vessel,
2 denotes the feed for the solid phase,
3 denotes the feed for the liquid phase,
4 denotes the feed for the atomising gas,
5 denotes the two-fluid nozzle,
6 denotes the feed for the fluidised gas,
7 denotes the fluidised bed,
8 denotes the settling zone in the fluidised bed,
9 denotes the counterflow gravity classifier, and
10 denotes the withdrawal device for the granules.

For carrying out the process according to the invention by means of variant (b), a solid mixture is first prepared by mixing at least one dispersant and, if appropriate, one or more agrochemical active compounds and/or additional compounds with at least one solid carrier in such a ratio that the resulting mixture is in the solid phase. This mixture of solid substances is homogenised and ground using customary processes.

Furthermore, a solution of at least one agrochemical active compound and, if appropriate, additional substances in at least one additive is prepared. For this purpose, the components are stirred with each other at temperatures between 10° C. and 100° C., preferably between 20° C. and 90° C., so that a liquid phase results. Accordingly, the liquid phase is a melt or a true solution.

For carrying out the process according to the invention by means of variant (b), the solid, finely pulverulent phase is passed into a mixer and sprayed with the liquid phase. In general, a procedure is followed, in which the liquid phase is sprayed into the mixer through one or more separate nozzles.

The liquid phase is preferably added via one or more two-fluid nozzles which are constructed in such a way that the liquid phase is transported through a first line and a stream of gas (atomising gas) is fed in through a second line. Both streams meet each other at the end of the nozzle in such a way that, with the aid of the atomising gas, the liquid phase is sprayed into the mixer in the form of small droplets, and there meets the particles of the solid phase.

If appropriate, a post-treatment can be carried out by spraying on water. To remove water and/or other solvents, the resulting solid formulation can be dried by customary methods.

When carrying out the process according to the invention by means of variant (b), the temperatures can also be varied within a substantial range. For example, the process is carried out using a liquid phase whose temperature is between 10° C. and 100° C., preferably between 20° C. and 90° C. The solid phase is kept at temperatures between 10° C. and 50° C., preferably between 20° C. and 40° C. The temperature of the stream of gas for atomisation, which enters through the two-fluid nozzle, is between 0° C. and 100° C., preferably between 10° C. and 90° C.

For spraying the liquid phase into the mixer via one or more nozzles, it is again possible to use all gases which are customary for such purposes. Air or nitrogen are preferably suitable.

For carrying out the process according to the invention by means of variant (b), all mixers are suitable which are customary for such purposes. The resulting solid formulation can be discharged from the mixer via customary withdrawal devices. The pulverulent or granular product obtained can subsequently be subjected to customary grinding or granulation.

When using variant (b), the process according to the invention can also be carried out continuously or discontinuously. In general, the process is carried out discontinuously by introducing the required components into the mixer in batches.

When carrying out the process according to the invention by means of variant (a), uniformly shaped granules are obtained, whereas pulverulent or granular products are obtained when using variant (b). These products can be comminuted by grinding by using devices which are customary for this purpose.

The solid formulations according to the invention have a high stability. They have a compact, microporous structure and are nevertheless spontaneously dispersible or soluble in water or other solvents. By spontaneous dispersibility, or solubility, is to be understood in the present case that the particles disperse, or dissolve, completely in generally 0.1 to 5 minutes, preferably in 0.2 to 3 minutes.

The solid formulations according to the invention contain one or more agrochemical active compounds and can therefore be employed using customary methods for the treatment of plants in agriculture and horticulture. The solid formulations according to the invention are, for example, dispersed in water. The dispersions formed in this process can be applied by customary methods to the plants and/or their environment, that is to say, for example, by spraying, atomising or pouring, if appropriate after previous dilution. The application rates in this context depend on the concentration of the dispersion, on the particular indication and on the active components employed.

The preparation and the use of the solid formulations according to the invention are illustrated by the examples which follow.

PREPARATION EXAMPLES

Example 1

To prepare a liquid phase, 930 g of 1-(4-chlorophenyl)-4,4-dimethyl-3-(1,2,4-triazol-1-yl-methyl)-pentan-3-ol (97%) are dissolved completely at 60° C. in 2700 g of polyethoxyisotridecyl alcohol having an average of 6 ethylene oxide units per molecule, with stirring.

Moreover, a finely pulverulent, solid phase is prepared by mixing 1200 g of a formaldehyde-crosslinked alkylarylsulphonate with 1170 g of highly disperse silica in a small plough-bar mixer at room temperature, and the mixture is homogenised.

The preparation of granules which follows is carried out in a fluidised-bed granulator. For this purpose, the solid phase is introduced into the granulator and fluidised by blowing in air at a temperature of 25° C. in an amount of 300 to 500 m$^3$/h. At the same time, spraying of the liquid phase at 60° C. into the fluidised bed via a two-fluid nozzle with the aid of air commences. After 60 minutes, spraying-in of the liquid phase is complete. After this, a post-granulation is carried out by spraying on 1600 g of water at 50° C., followed by drying to a residual moisture of 1% by weight of water by heating the air which is passed in at 70° C. The granules formed are classified. In this way, 5 kg of granules of particle sizes in the range between 200 and 1500 μm are obtained. When 1 kg of these granules, which contain 1.5% by weight of active compound, are added to 200 l of water, spontaneous wetting takes place, and the granules are dissolved completely within 10 seconds.

Example 2

To prepare a liquid phase, 1550 g of 1-(4-chlorophenyl)-4,4-dimethyl-3-(1,2,4-triazol-1-yl-methyl)-pentane-3-ol (97%) are dissolved completely in a mixture of 900 g of polyethoxy-iso-tridecyl alcohol having an average of 6 ethylene oxide units per molecule and 1200 g of alkylaryl-polyethoxy-ethanol phosphoric acid ester, which is commercially available under the name "Blendex®", at 60° C. with stirring.

Moreover, a finely pulverulent solid phase is prepared by mixing 1200 g of a formaldehyde-crosslinked alkylarylsulphonate with 1150 g of highly disperse silica in a small plough-bar mixer at room temperature and homogenising the mixture.

The preparation of granules which follows is carried out in a fluidised-bed granulator. For this purpose, the solid phase is introduced into the granulator and fluidised by blowing in air at a temperature of 25° C. in an amount of 300 to 500 m$^3$/h. At the same time, spraying of the liquid phase at 60° C. into the fluidised bed via a two-fluid nozzle with the aid of air commences. After 60 minutes, spraying-in of the liquid phase is complete. After this, post-granulation is carried out by spraying on 1600 g of water at 50° C., followed by drying to a residual moisture of 1% by weight of water by heating the air which is passed in at 70° C. The granules formed are classified. In this way, 5 kg of granules of particle sizes in the range between 200 and 1500 μm are obtained.

When 1 kg of these granules, which contain 2.5% by weight of active compound, are added to 200 l of water, spontaneous wetting takes place, and the granules are dissolved completely within 10 seconds.

EXAMPLE 3

To prepare a liquid phase, 4640 g of 1-(4-chlorophenyl)-4,4-dimethyl-3-(1,2,4-triazol-1-yl-methyl)-pentan-3-ol (97%) are dissolved completely in 13,360 g of polyethoxyisotridecyl alcohol with an average of 6 ethylene oxide units per molecule, at 60° C. with stirring.

Moreover, a finely pulverulent solid phase is prepared by mixing 6000 g of a formaldehyde-crosslinked alkylarylsulphonate with 6000 g of highly disperse silica in a small plough-bar mixer at room temperature and homogenising the mixture.

Granulation which then follows is carried out in a granulation apparatus of the type represented in FIG. 1. For this purpose, the solid phase is fed pneumatically to the fluidised-bed reactor via feedpipes 2 and fluidised by blowing in nitrogen at a temperature of 80° C., in an amount of 50 kg/h, via line 6. At the same time, the liquid phase at a temperature of 60° C., is sprayed in via the two-fluid nozzle 5 with the aid of nitrogen as the atomising gas. The streams of product are controlled in such a way that the solid phase is fed to the reactor in an amount of 1.2 kg/h and the liquid phase in an amount of 1.8 kg/h. From the fluidised bed 7 which forms, 3 kg/h of granules of an average particle size of 0.4 mm are continuously discharged via the counterflow gravity classifier 9 and the withdrawal device 10. In this manner, 28 kg of granules of a content of 15.0% by weight of 1-(4-chlorophenyl)-4,4-dimethyl-3-(1,2,4-triazol-1-yl-methyl)-pentan-3-ol are obtained.

EXAMPLE 4

To prepare a liquid phase 130 g of 6-methyl-2-oxo-1,3-dithiolo-[4,5-b]-quinoxaline are dissolved completely in 2500 g of polyethoxy-isotridecyl alcohol with an average of 6 ethylene oxide units per molecule and 2500 g of N-octyl-pyrrolidone, at 60° C. with stirring.

Moreover, a finely pulverulent solid phase is prepared by mixing 1000 g of rice starch and 1900 g of a formaldehyde-crosslinked alkylarylsulphonate with 1900 g of highly disperse silica in a small plough-bar mixer at room temperature and homogenising the mixture.

Granulation which then follows is carried out in a granulation apparatus of the type represented in FIG. 1. For this purpose, the solid phase is fed pneumatically to the fluidised-bed reactor via feedpipes 2 and fluidised by blowing in nitrogen at a temperature of 80° C., in an amount of 50 kg/h, via line 6. At the same time, the liquid phase at a temperature of 60° C., is sprayed in via the two-fluid nozzle 5 with the aid of nitrogen as the atomising gas. The streams of product are controlled in such a way that the solid phase is fed to the reactor in an amount of 1.2 kg/h and the liquid phase in an amount of 1.8 kg/h. From the fluidised bed 7 which forms, 3 kg/h of granules of an average particle size of 0.4 mm are continuously discharged via the counterflow gravity classifier 9 and the withdrawal device 10. In this manner, 9 kg of granules having a content of 1.3% by weight of 6-methyl-2-oxo-1,3-dithiolo-[4,5-b]-quinoxaline are obtained.

EXAMPLE 5

To prepare a liquid phase, 101.56 g of 1-(4-chlorophenyl)-4,4-dimethyl-3-(1,2,4-triazol-1-yl-methyl)-pentan-3-ol and 7.54 g of 6-methyl-2-oxo-1,3-dithiolo-[4,5-]-quinoxaline, 104.5 g of a mixture of N,N-dimethyl-alkylcarboxamides which consists, on average, of 5% of N,N-dimethyl-hexanecarboxamide, 50% of N,N-dimethyl-octanecarboxamide, 40% of N,N-dimethyl-decarboxamide and 5% of N,N-dimethyl-dodecanecarboxamide, 52.5 g of polyethoxy-isotridecyl alcohol with an average of 6 ethylene oxide units per molecule and 5 g of p-tolyl-sulphonic acid are completely dissolved with stirring at 80° C.

In addition, a finely pulverulent solid phase is prepared by mixing 156.5 g of highly disperse silica, 52.5 g of a diphenylsulphonic acid formaldehyde condensate and 19.9 g of sodium dialkylnaphthyl-sulphonate in a plough-bar mixer at room temperature and homogenising the mixture.

The preparation of the solid formulation which then follows is carried out in such a manner that the liquid phase is sprayed at 80° C. via a nozzle into the mixer onto the solid phase, which has a temperature equal to room temperature, while stirring. In this manner, 500 g of a granular solid formulation is obtained, which is ground to a powder.

EXAMPLE 6

To prepare a liquid phase, 136.64 g of 3-methyl-4-amino-6-phenyl-1,2,4-triazin-5(4H)-one and 30.0 g of polyethoxy-isotridecyl alcohol with an average of 6 ethylene oxide units per molecule are dissolved completely at 80° C. with stirring.

In addition, a finely pulverulent solid phase is prepared by mixing 18.32 g of 2-ethoxy-2,3-dihydro-3,3-dimethyl-5-benzofuranyl sulphonate, 18.60 g of 3-methoxycarbonyl-aminophenyl-N-(3'-methylphenyl)-carbamate, 60.0 g of a diphenylsulphonic acid formaldehyde condensate, 30.0 g of highly disperse silica and 6.44 g of kaolin in a plough-bar mixer at room temperature and homogenising the mixture.

The preparation of the solid formulation which then follows is carried out in such a manner that the liquid phase is sprayed at 80° C. via a nozzle into the mixer onto the solid phase, which has a temperature equal to room temperature, while stirring. In this manner, 300 g of a granular solid formulation is obtained, which is ground to a powder.

EXAMPLE 7

To prepare a liquid phase, 53.2 g kg of 1-(4-chlorophenoxy)-3,3-dimethyl-1-(1,1,4-triazol-1-yl)-butan-2-one, 20 kg of polyethoxy-isotridecyl alcohol with an average of 6 ethylene oxide units per molecule, 20 kg of N-octyl-pyrrolidone and 20 kg of a mixture of N,N-dimethyl-alkylcarboxamides which consists, on average, of 5% of N,N-dimethyl-hexanecarboxamide, 50% of N,N-dimethyl-octanecarboxamide, 40% of N,N-dimethyl-decanecarboxamide and 5% of N,N-dimethyl-dodecanecarboxamide, are dissolved completely at 90° C. with stirring.

In addition, a finely pulverulent solid phase is prepared by mixing 4 kg of a wetting agent based on alkylaryl-sulphonate, 20 kg of a diphenyl-sulphonic acid formaldehyde condensate and 62.8 kg of highly disperse silica in a plough-bar mixer at room temperature and homogenising the mixture.

The preparation of the solid formulation which then follows is carried out in such a manner that the liquid phase is sprayed at 90° C. via a nozzle into the mixer onto the solid phase, which has a temperature equal to room temperature, while stirring. In this manner, 200 kg of a granular solid formulation is obtained, which is ground to a powder.

Example 8

To prepare a liquid phase, 26.3 kg of 1-(4-chlorophenoxy)-3,3-dimethyl-1-(1,1,4-triazol-1-yl)-butan-2-ol, 10 kg of polyethoxy-isotridecyl alcohol with an average of 6 ethylene oxide units per molecule, 10 kg of N-octyl-pyrrolidone and 10 kg of a mixture of N,N-dimethyl-alkylcarboxamides which consists, on average, of 5% of N,N-dimethyl-hexanecarboxamide, 50% of N,N-dimethyl-octanecarboxamide, 40% of N,N-dimethyl-decanecarboxamide and 5% of N,N-dimethyl-dodecanecarboxamide, are dissolved completely at 90° C. with stirring.

In addition, a finely pulverulent solid phase is prepared by mixing 2 kg of a wetting agent based on alkylaryl-sulphonate, 10 kg of a diphenyl-sulphonic acid formaldehyde condensate and 31.7 kg of highly disperse silica in a plough-bar mixer at room temperature and homogenising the mixture.

The preparation of the solid formulation which then follows is carried out in such a manner that the liquid phase is sprayed at 90° C. via a nozzle into the mixer onto the solid phase, which has a temperature equal to room temperature, while stirring. In this manner, 100 kg of a granular solid formulation is obtained, which is ground to a powder.

Example 9

To prepare a liquid phase, 25.5 kg of 1-(4-chlorophenyl)-4,4-dimethyl-3-(1,2,4-triazol-1-yl-methyl)-pentan-3-ol, 10 kg of polyethoxy-isotridecyl alcohol with an average of 6 ethylene oxide units per molecule, 10 kg of N-octyl-pyrrolidone and 10 kg of a mixture of N,N-dimethyl-alkylcarboxamides which consists, on average, of 5% of N,N-dimethyl-hexanecarboxamide, 50% of N,N-dimethyl-octanecarboxamide, 40% of N,N-dimethyl-decanecarboxamide and 5% of N,N-dimethyl-dodecanecarboxamide, are dissolved completely at 90° C. with stirring.

In addition, a finely pulverulent solid phase is prepared by mixing 2 kg of a wetting agent based on alkylaryl-sulphonate, 10 kg of a diphenyl-sulphonic acid formaldehyde condensate and 32.5 kg of highly disperse silica in a plough-bar mixer at room temperature and homogenising the mixture.

The preparation of the solid formulation which then follows is carried out in such a manner that the liquid phase is sprayed at 90° C. via a nozzle into the mixer onto the solid phase, which has a temperature equal to room temperature, while stirring. In this manner, 100 kg of a granular solid formulation is obtained, which is ground to a powder.

Example 10

To prepare a liquid phase, 10 g of 1-[4-(2-chloro-1,1,2-trifluoroethoxy)-phenyl]-3-(4-phenyl-1,2,5-oxadiazol-3-yl)-urea, 30 g of an emulsifier based on alkylarylpolyglycol ether, 6 g of an ethyleneoxide-dimethylsiloxane block copolymer with Si-C-bonds, 6 g of the sodium salt of coconut fatty acid 2-sulfethylester containing 10% of free coconut fatty acid are dissolved completely at 90° C. with stirring.

In addition, a finely pulverulent solid phase is prepared by mixing 12 g of a diphenyl-sulphonic acid formaldehyde condensate and 36 g of highly disperse silica in a mixer at room temperature and homogenising the mixture.

The preparation of the solid formulation which then follows is carried out in such a manner that the liquid phase is sprayed at 90° C. via a nozzle into the mixer onto the solid phase, which has a temperature equal to room temperature, while stirring. In this manner, 100 g of a granular solid formulation is obtained, which is ground to a powder.

Comparison example A

A mixture of 2630 g of 1-(4-chlorophenyl)-4,4-dimethyl-3-(1,2,4-triazol-1-yl-methyl)-pentan-3-ol, 2000 g of a formaldehyde-crosslinked alkylarylsulphonate, 300 g of phospholipid and 5070 g of sodium hydrogen carbonate is comminuted in a plough-bar mixer to a particle size of about 1 mm, and the mixture is homogenised. The mixture is then ground with the aid of an air-jet mill to an average particle size of about 7 μm and remixed.

The resulting premix is processed in a commercially available fluidised-bed granulator to give granules by moistening batches of 4.8 kg of powder in the fluidised bed with 1.5 liters of water in the course of 21 minutes at room temperature and subsequently drying the granules by warming the inlet air to 70° C. in the course of 11 minutes, so that the residual water content in the granules is about 1% by weight. The temperature of the granules in this procedure remains below 40° C. The resulting granules are classified using a cascade of vibrating screens. In this manner, 4.5 kg of granules having particle sizes in the range between 200 and 1500 μm are obtained per batch.

The suspension stability of the granules, measured by CIPAC method MT 168, is 84%. The wet-screen test on screens with mesh size 315, 250 and 160 μm, respectively, carried out by CIPAC method MT 167 gives screening residues of less than 0.005%.

Comparison example B

A mixture of 2630 g of 1-(4-chlorophenyl)-4,4-dimethyl-3-(1,2,4-triazol-1-yl-methyl)-pentan-3-ol, 2000 g of a formaldehyde-crosslinked alkylarylsulphonate, 300 g of phospholipid and 5070 g of sodium hydrogen carbonate is stirred into 10 kg of water with the aid of a toothed-disk stirrer and the mixture is precomminuted with a toothed colloid mill. It is then ground finely on a bead mill whose throughput is 25 kg/h. An aqueous suspension of a solids content of 50% by weight is obtained. At a shear gradient of 1000/sec, the viscosity of the suspension is approx. 65 mPas; the average particle diameter is approx. 4 μm.

In an amount of 7 kg/h, the resulting suspension is sprayed through nozzles into a fluidised-bed reactor with continuously classifying product discharge. A stream of nitrogen in an amount of 92 kg/h is used for fluidising. The temperature of the stream of nitrogen is 90° C. In the fluidised bed which forms, a product temperature of below 40° C. is established. The granules discharged have a particle size of approx. 0.4 mm. The residual moisture of the granules is 2.1% by weight of water.

The suspension stability of the granules, measured by CIPAC method MT 168, is 98%. The wet-screen test on screens with mesh size 315, 250 and 160 μm, respectively, carried out by CIPAC method MT 167, gives no screening residues.

In the use examples which follow, the granules prepared were tested for their biological effectiveness.

Use Example A

Erysiphe Test (barley)/curative

To prepare a suitable preparation of active compound, 1 part by weight of the particular granules is mixed with water, and the resulting concentrate is diluted with water to the desired concentration.

To test for curative effectiveness, young plants are dusted with spores of Erysiphe graminis f. sp. hordei. 48 hours after the inoculation, the plants are sprayed with the preparation of active compound until dew-moist.

The plants are placed in a greenhouse at a temperature of approx. 20° C. and a relative atmospheric humidity of approx. 80% to allow the development of mildew pustules.

The evaluation is carried out 7 and 14 days after the inoculation.

The formulations and concentrations of active compound, and the test results, can be seen from the table below.

TABLE A

Erysiphe Test (barley)/curative

| Granules of Example | Active compound concentration in the spray mixture in mg/l | Degree of effectiveness in % of the untreated control | |
|---|---|---|---|
| | | 7d | 14d |
| Known: | | | |
| (A) | 150 | 0 | 0 |
| (B) | 150 | 0 | 0 |
| According to the invention | | | |
| (1) | 150 | 80 | 75 |
| (2) | 150 | 49 | 15 |
| (3) | 150 | 88 | 60 |

It will be understood that the specification and examples are illustrative but not limitative of the present invention and that other embodiments within the spirit and scope of the invention will suggest themselves to those skilled in the art.

What is claimed is:

1. A solid formulation for application to plants or to their habitat consisting essentially of
   A) at least one agrochemically active compound selected from the group consisting of
      i) a fungicide selected from the group consisting of
         1-(4-chlorophenyl)-4,4-dimethyl-3-(1,2,4-triazol-1-yl-methyl)-pentan-3-ol (tebuconazole),
         1-(4-chlorophenoxy)-3,3-dimethyl-1-(1,2,4-triazol-1-yl)-butan-2-ol (triadimenol),
         1-(4-chlorophenoxy)-3,3-dimethyl-1-(1,2,4-triazol-1-yl)-butan-2-one (triadimefon),
         1-(4-phenyl-phenoxy)-3,3-dimethyl-(1,2,4-triazol-1-yl)-butane-2-ol (bitertanol),
         N,N-dimethyl-N'-phenyl-(N'-fluorodichloromethylthio)-sulphamide (dichlofluanid), N,N-dimethyl-(N'-fluorodichloromethylthio)-N'-(4-methylphenyl)-sulphamide (tolylfluanid),
N-trichloromethylmercapto-4-cyclohexene-1,2-dicarboxamide (captan),
N-(1,1,2,2-tetrachloroethyl-sulphenyl)-cis-4-cyclohexene-1,2-dicarboxamide (captafol),
N-trichloromethylthio-phthalimide (folpet),
N-dodecyl-quanidine acetate (dodine),
tetrachloro-isophthalonitrile (chlorothalonil),
4,5,6,7-tetrachlorophthalide,
zinc ethylene-bis-dithiocarbamate (zineb),
manganese ethylene-bis-dithiocarbamate (maneb),
zinc ethylene-bis-dithiocarbamate/manganese ethylene-bis-dithiocarbamate (mancozeb),
zinc propylene-1,2-bis-dithiocarbamate (propineb),
1-[3-(4-(1,1-dimethylethyl)-phenyl)-2-methyl-propyl]piperidine (fenpropidin),
N-tridecyl-2,6-dimethyl-morpholine (tridemorph),
N-dodecyl-2,6-dimethyl-morpholine (aldimorph),
2-[2-(2,4-dichlorophenyl)-2-(2-propenyloxy)-ethyl]-imidazole (imazalil),
N-[2-(2,4,6-trichlorophenoxy)-ethyl]-N-propyl-1H-imidazole (prochloraz),
N-(3,5-dichlorophenyl)-1,2-dimethyl-cyclopropane-1,2-dicarboximide (procymidone),
2-methoxycarbamoyl-benzimidazole (carbendazim),
methyl 1-(butylcarbamoyl)-2-benzimidazolecarbamate (benomyl),
2,4-dichloro-6-(2'-chlorophenyl-amino)-1,3,4-triazine (anilazine),
bis-(8-guanidino-octyl)-amine triacetate (guazatine),
1-(4-chlorobenzyl)-1-cyclopentyl-3-phenyl-urea (pencycuron),
6-methyl-2-oxo-1,3-dithiolo-[4,5-b]-quinoxaline (chinomethionat),
1-(4-fluorophenyl)-1-(1,2,4-triazol-1-yl-methyl)-2-(2-chlorophenyl)-oxirane,
2-(2,4-dichlorophenyl)-1-(1,2,4-triazol-1-yl)-pentane (penconazole),
1-[2-(2,4-dichlorophenyl)-4-propyl-1,3-dioxolan-2-yl-methyl]-1H-(1,2,4-triazole) (propiconazole),
1-(2-[2-chloro-4-(4-chlorophenoxy)-phenyl]-4-methyl-(1,3-dioxolan-2-yl)-methyl]-1H-(1,2,4-triazole),
1-(2,4-dichlorophenyl)-4,4-dimethyl-2-(1,2,4-triazol-1-yl)-pentan-3-ol (diclobutrazole) and
1-(2-chlorophenyl)-2-(1-chloro-cyclopropyl)-3-(1,2,4-triazol-1-yl)-propan-2-ol,
ii) a herbicide selected from the group consisting of
4-amino-6-(1,1-dimethyl-ethyl)-3-methylthio-1,2,4-triazin-5(4H)-on (metribuzin),
3-methyl-4-amino-6-phenyl-1,2,4-triazin-5(4H)-on (metamitron), and
N-benzthiazolyl-N-methyl-N'-methyl-urea and
3-methoxycarbonyl-aminophenyl-N-(3'-methyl-phenyl)carbamate,
iii) an insecticide selected from the group consisting of 2-isopropoxy-phenyl-N-methylcarbamate,
N-(4-trifluoromethoxy-phenyl)-N'-(2-chlorobenzoyl)urea,
1-[4-(2-chloro-1,1,2-trifluoroethoxy)-phenyl]-3-(4-phenyl-1,2,5-oxadiazol-3-yl)-urea and
2-ethoxy-2,3-dihydro-3,3-dimethyl-5-benzofuranylmethansulfonate,
iv) trans-4-(4-chlorophenyl)-N-cyclohexyl-4-methyl-2-oxo-3-thiazolidin-carboxamide (hexythiazox) and
v) 1-cyclohexyl-4,4-dimethyl-3-hydroxy-2-(1,2,4-triazol-1-yl)-pent-1-ene (triapenthenol),
B) at least one additive selected from the group consisting of
i) polyethoxy-isotridecylalcohol having an average of 6 ethylene oxide units per molecule,
ii) an alkylaryl-polyethoxyethanol phosphoric acid ester,
iii) an N-alkyl-lactam of the formula

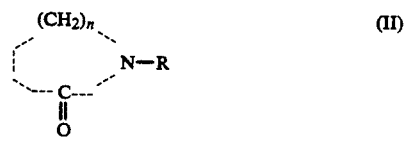

in which
R represents alkyl having 6 to 18 carbon atoms and
n represents the numbers 3, 4 or 5, and
iv) an N,N-dimethyl-alkylcarboxamide of the formula

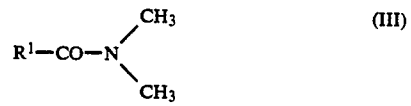

in which
R¹ represents alkyl having 5 to 11 carbon atoms,
c) at least one dispersant selected from the group consisting of ligninsulphonates, condensation products of aryl- or alkylaryl-sulphonic acids and formaldehyde, and addition products of ethyleneoxide and fatty acid esters and salts thereof, and
d) at least one carrier selected from the group consisting of ground natural minerals, ground synthetic materials and salts.

2. A method for treating plants which method comprises applying to the plants or to their habitat an effective amount of a formulation according to claim 1.

3. A formulation according to claim 1, wherein the agrochemical active compound is a fungicide selected from the group consisting of
1-(4-chlorophenyl)-4,4-dimethyl-3-(1,2,4-triazol-1-yl-methyl)-pentan-3-ol (tebuconazole),
1-(4-chlorophenoxy)-3,3-dimethyl-1-(1,2,4-triazol-1-yl)-butan-2-ol (triadimenol),
1-(4-chlorophenoxy)-3,3-dimethyl-1-(1,2,4-triazol-1-yl)-butan-2-one (triadimefon),
1-(4-phenyl-phenoxy)-3,3-dimethyl-(1,2,4-triazol-1-yl)-butane-2-ol (bitertanol),
N,N-dimethyl-N'-phenyl-(N'-fluorodichloromethyl-thio)-sulphamide (dichlofluanid),
N,N-dimethyl-(N'-fluorodichloromethylthio)-N'-(4-methylphenyl)-sulphamide (tolylfluanid),
N-trichloromethylmercapto-4-cyclohexene-1,2-dicarboxamide (captan),
N-(1,1,2,2-tetrachloroethyl-sulphenyl)-cis-4-cyclohexene-1,2-dicarboxamide (captafol), N-trichloromethylthio-phthalimide (folpet),
N-dodecyl-guanidine acetate (dodine),
tetrachloro-isophthalonitrile (chlorothalonil),
4,5,6,7-tetrachlorophthalide,
zinc ethylene-bis-dithiocarbamate (zineb),
manganese ethylene-bis-dithiocarbamate (maneb),
zinc ethylene-bis-dithiocarbamate/manganese ethylene-bis-dithiocarbamate (mancozeb),
zinc propylene-1,2-bis-dithiocarbamate (propineb),
1-[3-(4-(1,1-dimethylethyl)-phenyl)-2-methylpropyl]-piperidine (fenpropidin),
N-tridecyl-2,6-dimethyl-morpholine (tridemorph),
N-dodecyl-2,6-dimethyl-morpholine (aldimorph),
2-[2-(2,4-dichlorophenyl)-2-(2-propenyloxy)-ethyl]-imidazole (imazalil),
N-[2-(2,4,6-trichlorophenoxy)-ethyl]-N-propyl-1H-imidazole (prochloraz),
N-(3,5-dichlorophenyl)-1,2-dimethyl-cyclopropane-1,2-dicarboximide (procymidone),
2-methoxycarbamoyl-benzimidazole (carbendazim),
methyl 1-(butylcarbamoyl)-2-benzimidazolecarbamate (benomyl),
2,4-dichloro-6-(2'-chlorophenyl-amino)-1,3,4-triazine (anilazine),
bis-(8-guanidino-octyl)-amine triacetate (guazatine),
1-(4-chlorobenzyl)-1-cyclopentyl-3-phenyl-urea (pencycuron),
6-methyl-2-oxo-1,3-dithiolo-[4,5-b]-quinoxaline (chinomethionat),
1-(4-fluorophenyl)-1-(1,2,4-triazol-1-yl-methyl)-2-(2-chlorophenyl)-oxirane,
2-(2,4-dichlorophenyl)-1-(1,2,4-triazol-1-yl)-pentane (penconazole),
1-[2-(2,4-dichlorophenyl)-4-propyl-1,3-dioxolan-2-yl-methyl]-1H-(1,2,4-triazole) (propiconazole),
1-(2-[2-chloro-4-(4-chlorophenoxy)-phenyl]-4-methyl-(1,3-dioxolan-2-yl)-methyl]-1H-(1,2,4-triazole),
1-(2,4-dichlorophenyl)-4,4-dimethyl-2-(1,2,4-triazol-1-yl)-pentan-3-ol (diclobutrazole) and
1-(2-chlorophenyl)-2-(1-chloro-cycloprop-1-yl)-3-(1,2,4-triazol-1-yl)-propan-2-ol.

4. A formulation according to claim 1, wherein the agrochemical active compound is a herbicide selected from the group consisting of
4-amino-6-(1,1-dimethyl-ethyl)-3-methylthio-1,2,4-triazin-5(4H)-on (metribuzin),
3-methyl-4-amino-6-phenyl-1,2,4-triazin-5(4H)-on (metamitron),
N-benzthiazolyl-N-methyl-N'-methyl-urea and
3-methoxycarbonyl-aminophenyl-N-(3'-methyl-phenyl)-carbamate, 5. A formulation according to claim 1, wherein the agrochemical active compound is an insecticide selected from the group consisting of 2-isopropoxyphenyl-N-methyl-carbamate,
N-(4-trifluoromethoxy-phenyl)-N-(2-chloro-benzoyl)-urea,
1-[4-(2-chloro-1,1,2-trifluoroethoxy)-phenyl]-3-(4-phenyl-1,2,5-oxadiazol-3-yl)-urea and
2-ethoxy-2,3-dihydro-3,3-dimethyl-5-benzofuranylmethansulfonate.

6. A formulation according to claim 1, wherein the agrochemical active compound is trans-4-(4-chlorophenyl)-N-cyclohexyl-4-methyl-2-oxo-3-thiazolidin-carboxamide (hexythiazox).

7. A formulation according to claim 1, wherein the agrochemical active compound is 1-cyclohexyl-4,4-dimethyl-3-hydroxy-2-(1,2,4-triazol-1-yl)-pent-1-ene (triapenthenol).

8. A formulation according to claim 1, wherein B is an N-alkyl-lactam of the formula (II), in which
R represents alkyl having 8, 10 or 12 carbon atoms and
n represents the numbers 3, 4 or 5.

9. A formulation according to claim 1, wherein (B) is a mixture of N,N-dimethyl-alkylcarboxamides comprising on average 5% of N,N-dimethylhexanecarboxamide, 50% of N,N-dimethyl-octanecarboxamide, 40% of N,N-dimethyl-decanecarboxamide and 5% of N,N-dimethyl-dodecanecarboxamide.

10. A composition according to claim 1, further containing (E) at least one additive selected from the group consisting of binders, preservatives, colorants, acids and granulation liquids.

11. A composition according to claim 1, wherein (A) is 1-(4-chlorophenyl)-4,4-dimethyl-3-(1,2,4-triazol-1-yl-methyl)-pentan-3-ol and (B) is polyethoxyisotridecyl alcohol having an average of 6 ethylene oxide units per molecule.

12. A composition according to claim 1, wherein (A) is 1-(4-chlorophenyl)-4,4-dimethyl-3-(1,2,4-triazol-1-yl-methyl)-pentan-3-ol and (B) is a mixture of polyethoxyisotridecyl alcohol having an average of 6 ethylene oxide units per molecule and of alkylaryl-polyethoxyethanol phosphoric acid ester.

13. A composition according to claim 1, wherein (A) is 6-methyl-2-oxo-1,3-dithiolo-[4,5-b]-quinoxaline and (B) is polyethoxy-isotridecyl alcohol with an average of 6 ethylene oxide units per molecule.

14. A composition according to claim 1, wherein (A) is 1-(4-chlorophenyl)-4,4-dimethyl-3-(1,2,4-triazol-1-yl-methyl)-pentan-3-ol and 6-methyl-2-oxo-1,3-dithiolo-[4,5-b]-quinoxaline, and (B) is a mixture of N,N-dimethyl-alkylcarboxamides which consists, on average, of 5% of N,N-dimethyl-hexanecarboxamide, 50% of N,N-dimethyl-octanecarboxamide, 40% of N,N-dimethyl-decanecarboxamide and 5% of N,N-dimethyl-dodecanecarboxamide.

15. A composition according to claim 1, wherein (A) is 3-methyl-4-amino-6-phenyl-1,2,4-triazin-5(4H)-one and (B) is polyethoxy-isotridecyl alcohol with an average of 6 ethylene oxide units per molecule.

16. A composition according to claim 1, wherein (A) is 1-(4-chlorophenyl)-3,3-dimethyl-1-(1,1,4-triazol-1-yl)-butan-2-one, and (B) is a mixture of polyethoxy-isotridecyl alcohol with an average of 6 ethylene oxide units per molecule, N-octyl-pyrrolidone and a mixture of N,N-dimethyl-alkylcarboxamides which consists, on average, of 5% of N,N-dimethyl-hexanecarboxamide, 50% of N,N-dimethyl-octanecarboxamide, 40% of N,N-dimethyl-decanecarboxamide and 5% of N,N-dimethyl-dodecanecarboxamide.

17. A composition according to claim 1, wherein (A) is 1-(4-chlorophenoxy)-3,3-dimethyl-1-(1,1,4-triazol-1-yl-butan-2-ol, and (B) is a mixture of polyethoxy-isotridecyl alcohol with an average of 6 ethylene oxide units per molecule, N-octyl-pyrrolidone and a mixture of N,N-dimethyl-alkylcarboxamides which consists, on average, of 5% of N,N-dimethyl-hexanecarboxamide, 50% of N,N-dimethyl-octanecarboxamide, 40% of N,N-dimethyl-decanecarboxamide and 5% of N,N-dimethyl-dodecanecarboxamide.

18. A composition according to claim 1, wherein (A) is 1-(4-chlorophenyl)-4,4-dimethyl-3-(1,2,4-triazol-1-yl-methyl)-pentan-3-ol and (B) is a mixture of polyethoxyisotridecyl alcohol with an average of 6 ethylene oxide units per molecule, N-octyl-pyrrolidone and a mixture of N,N-dimethyl-alkylcarboxamides which consists, on average, of 5% of N,N-dimethyl-hexanecarboxamide, 50% of N,N-dimethyl-octanecarboxamide, 40% of N,N-dimethyl-decanecarboxamide and 5% of N,N-dimethyl-dodecanecarboxamide.

19. A composition according to claim 1, wherein (A) is 1-[4-(2-chloro-1,1,2-trifluoroethoxy)-phenyl]-3-(4-phenyl-1,2,5-oxadiazol-3-yl)-urea.

* * * * *